United States Patent [19]
Clouser et al.

[11] 4,254,654
[45] Mar. 10, 1981

[54] MODULATED FLUID DETECTOR

[75] Inventors: David E. Clouser, Wilmington, Del.; John S. Craven, West Grove, Pa.

[73] Assignee: Hewlett-Packard Company, Palo Alto, Calif.

[21] Appl. No.: 730,559

[22] Filed: Oct. 7, 1976

[51] Int. Cl.³ .................................................. G01N 31/08
[52] U.S. Cl. ................................................................ 73/27 R
[58] Field of Search ................ 73/23.1, 27 R, 1 G, 73/204; 23/232 C, 254 R

[56] References Cited

U.S. PATENT DOCUMENTS

| | | | |
|---|---|---|---|
| 1,954,681 | 4/1934 | Oetjen | 73/27 R |
| 2,255,551 | 9/1941 | Willenborg | 73/27 R |
| 3,050,983 | 8/1962 | Gohlke | 73/27 R |
| 3,084,536 | 4/1963 | McNabb | 73/27 R |
| 3,087,112 | 4/1963 | Pfefferle | 73/23.1 |
| 3,924,442 | 12/1975 | Kerho et al. | 73/1 G |
| 3,863,489 | 2/1975 | Ayers et al. | 73/23.1 |

FOREIGN PATENT DOCUMENTS 728194 10/1942 Fed. Rep. of Germany .......... 73/27 R

OTHER PUBLICATIONS

Palmer et al., Thermal Conductivity Method for Analysis of Gases, pp. 36-39, 42, 47, 1924.

Primary Examiner—Stephen A. Kreitman
Attorney, Agent, or Firm—Donald N. Timbie

[57] ABSTRACT

A sample fluid and a reference fluid are alternately applied to a fluid detector and an output signal is derived that is proportional to the difference between the response of the detector to the fluids.

14 Claims, 7 Drawing Figures

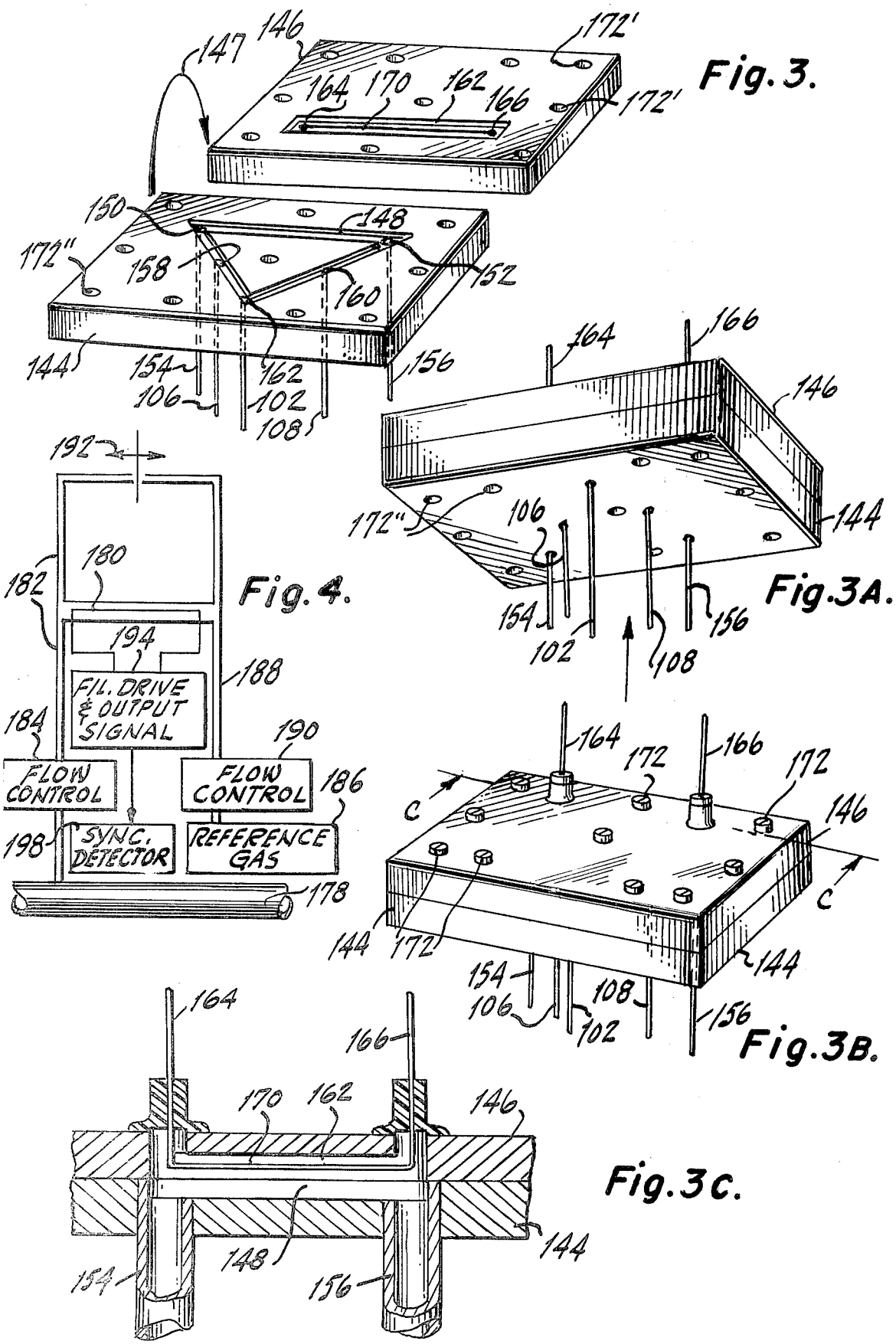

MODULATED FLUID DETECTOR

BACKGROUND OF THE INVENTION

Liquid and gas chromatographs are widely used to measure the relative concentrations of chemicals in a mixture. They are extremely sensitive. In operation, a small sample of the mixture to be analyzed is injected into a steady flow of carrier medium just as it enters a long thin tube known as a column. Due to action of material in the column, each chemical emerges from the column during a different interval following the time of injection. Inasmuch as the time it takes each chemical to pass through a given column is known from previous experiment, the identity of a chemical emerging during a given interval is established.

A detector that produces an electrical signal proportional to the intensity of a characteristic of matter flowing through it is connected to receive the effluent from the column. The carrier medium is selected so as to have a significantly different intensity of the characteristic per unit mass than the chemicals being analyzed. Accordingly, when the effluent from the column consists of pure carrier medium, the signal produced by the detector has a predetermined value termed the baseline. During the intervals when the effluent from the column contains one of the chemicals being measured, the signal gradually moves above or below the baseline in the form of a peak. The area between the peak and the baseline measured by an integrator and is proportional to the amount of the chemical in the sample.

The temperature of the column is controlled in an oven. The material contained in the column bleeds, i.e., it puts chemicals of its own into the flow of carrier medium. If this occurs at a steady rate, as it does when the temperature of the column is kept steady, the only effect is to shift the baseline by a constant amount and does not present a problem. This is known as isothermal operation.

However, when certain chemicals are being analyzed, optimum separation between the intervals during which they emerge from the column is only attained by programming the temperature of the oven. This changes the amount of column bleed and causes the baseline to drift by varying amounts so that it is difficult for the integrator to determine the area of a peak that is due to the presence of a chemical being measured.

For as long as fifteen years the solution to this problem has been the use of what is known as dual column operation. Two columns are mounted in the oven and a separate detector is provided for each. Equal flow of identical carrier medium is introduced into each column but the sample of chemicals is injected into only one. The amount of carrier medium and column bleed from each column is ideally the same. If the detectors are identical, the baseline signals of each are the same and the only difference in the signals provided by the detectors is due to the presence of the sample of chemicals being analyzed. Therefore, if the signals from the detectors are subtracted, a signal is derived that represents the concentrations of the various chemicals in the sample.

Whereas this method tends to cancel the deleterious effects of column bleed, it makes no correction for the differences in the responses of the detectors employed. This is especially important when it is desired to use a thermal conductivity detector because in spite of great expense and care in manufacture as well as selection, it is difficult to attain a precisely matched pair of detectors. Even if initial match is achieved, it is generally lost during operation or for that matter while the detectors are sitting on the shelf due to ageing. In an effort to provide matched pairs of thermal conductivity detectors, both have been inserted into a single large specially constructed metal block. Before accurate results can be attained, all parts of the block must reach the same temperature, and this requires as much as twelve hours.

The thermal conductivity detector has many advantageous characteristics, including low cost, but it is so adversely affected by ambient conditions, in spite of the large block, that its use is limited.

BRIEF DESCRIPTION OF EMBODIMENTS OF THE INVENTION

In accordance with this invention a single detector is used and the flow through it is switched so as to alternate between a carrier medium containing a sample of the chemicals of interest and a carrier medium alone. Means are provided for deriving an output signal proportional to the difference between the signals provided by the detector during the alternate halves of the switching cycle.

Thus, during dual column operation the effluent from the column into which the sample is injected is caused to flow through the detector during one half-cycle of the switching frequency and the effluent from the other column is caused to flow through the detector during the other half-cycle.

In single column operation, the detector is alternately supplied by a suitable switching means with effluent from the column containing the injected sample during one half-cycle and carrier medium alone during the other half-cycle. The carrier medium can be provided either directly from the same source supplying the sample column, or, as in dual column operation, indirectly through another column subjected to the same temperature as the first. Means are provided for deriving a signal proportional to the difference in the signals of the detector during successive halves of the switching cycle.

The invention can also be used in monitoring the flow of chemicals in a pipeline. A small portion of the pipeline flow is made to pass through a detector during one half of a switching cycle and reference medium is made to pass through the detector during the other half-cycle. Once again, means are provided for deriving the difference in the signals of the detector occurring during successive half-cycles. If the reference medium is the same as the flow in the pipeline, the difference signal will be zero, but if the characteristic of the material in the pipeline changes, the signal will have an alternating current component at the switching frequency that can be used merely as an indication or as a means of control in servo loop. In a similar manner the invention can be used to detect leaks by comparing air in the vicinity of a possible leak with nearby ambient air.

Therefore, this invention requires only one detector instead of two in dual column operations and makes it possible to use T.C. detectors in both dual and single column operation under conditions that would suggest the use of a different detector. Furthermore, the T.C. detector can be relatively simple and inexpensive to manufacture because variations in its output signal due to ambient conditions are eliminated. And, because only one detector is used, there is, of course, no need to match detectors.

One other feature of this invention is of importance. It has been found by feeding the T.C. detector from one end of the cell with the carrier medium containing the sample and from the other end of the cell with the carrier medium alone, that the noise due to flow variations is reduced to one eighth of that experienced in conventional systems. In alternating the flow through a detector as briefly described, it is possible to utilize mechanical switching means in the path of the flow, but if the sample chemicals are corrosive, the switch can be damaged. Therefore, means are provided for alternately switching the flow through the detector in such manner that no mechanical parts are exposed to the corrosive action of the two sample chemicals. Briefly, this is attained by utilizing hydraulic pressures.

THE DRAWINGS

FIG. 1 illustrates a gas chromatograph having a thermal conductivity detector with a cell that is alternately fed with sample gas and reference gas at one end.

FIG. 2 illustrates a gas chromatograph having a thermal conductivity detector with a cell that is alternately fed with sample gas at one end and reference gas at the other, FIG. 3 is a perspective view of the inner surfaces of the plates that form a thermal conductivity cell constructed in accordance with this invention and useful in the gas chromatograph shown in FIG. 2, FIGS. 3A and 3B are external views of the plates of FIG. 3, when assembled, FIG. 3C is a section CC of a portion of FIG. 3B, and FIG. 4 illustrates the use of a mechanical switch in a system wherein the invention is used to monitor the flow in a pipeline.

DESCRIPTION OF ONE EMBODIMENT OF THE INVENTION

In the chromotograph of FIG. 1 a single column gas chromatograph is shown. A storage tank 2 contains a gas that is used as reference gas and as carrier gas. A mass flow controller 4 is connected between the tank 2 and a column 6, and a carefully measured quantity of chemicals to be analyzed is injected into the head of the column 6 by a sample injector 8. As previously stated, the column 6 separates the different chemicals from each other on a time basis so that the effluent from the column appears as indicated by the graph 10 in which the baseline 11 is due to the carrier gas and any gas given off by the column. The first chemical to emerge is indicated by the peak 12, and the others by the successive peaks 14, 16, and 18. The shaded area between the peaks and the baseline 11 is a measure of the quantity of the chemical in the sample. From previous experience with a column of a given construction, and under given conditions, it is known how long each particular chemical takes to pass through the column and therefore the chemical represented by each of the peaks 12-18 can be determined.

The effluent from the column 6 flows into a tube 20 at a junction 22. One end of the tube 20 is connected via an hydraulic resistive coil 24 to a vent 26, which is generally the atmosphere. The other end of the tube 20 is connected via an hydraulic resistive coil 28 to a detector contained within the dotted rectangle 30. Switching of the effluent from the column 6 to the vent 26 or to the detector 30 is selectively controlled in the following way. Gas, which we will now refer to as reference gas, is conducted from the tank 2 by a tube 32 to the inputs of two pressure regulators 34 and 36. The output of the regulator 34 is coupled by a valve 42 into the tube 20 at a point 43 that is intermediate the junction 22 and the hydraulic resistive element 24. The output of the pressure regulator 36 is coupled via a valve 44 into the tube 20 at a point 45 that is intermediate the junction 22 and the hydraulic resistive element 28.

With the valve 42 open and the valve 44 closed, as illustrated, pressure of the reference gas at the point 43 can be made by the regulator 34 to be sufficient to force the effluent from the column 6 through the hydraulic resistive element 28 into the detector 30. When, however, the valve 42 is closed and the valve 44 open, the pressure at the point 45 may be made such as to force the effluent from the column 6 out the vent 26. In this case the reference gas alone flows into the detector 30. Any suitable valve driving circuit such as 46 can be used to control the valves 42 and 44 in such manner that one is shut while the other is open and vice versa. The choice of the switching frequency at which the valves are operated will be discussed below, but a frequency of about 10 Hz has been found satisfactory. Whatever frequency is chosen can be derived by energizing the valve driving circuit from a frequency source 48. Thus, the structure just described is a switching means for causing the flow through the detector 30 to alternate between effluent from the column 6 and reference gas.

With the detector 30 alternately supplied with column effluent and reference gas, in the manner just described, its electrical output signal will alternate at the switching frequency between a value corresponding to a characteristic of the sample gas eluting from the column 6 and a value corresponding to the same characteristic of the reference gas alone. The difference in these signals is due to the chemical gases being analyzed that are present in the sample gas but not in the reference gas. Both signals, however, will be equally affected by factors that gradually change the output signals of the detector. Therefore, the effect of these latter factors can be eliminated if the signals resulting from the sample gas are subtracted from the signals resulting from the reference gas or vice versa.

Various means are known to those skilled in the art for performing the subtraction. In FIG. 1 the output of the detector 30 is applied to a synchronous detector 52 where it is mixed with a constant amplitude signal of the switching frequency derived from the output of the frequency source 48. A signal delay means 54 is connected between the frequency source 48 and the synchronous detector 52 so as to compensate for any delay resulting from the action of the detector 30, thereby insuring that the switching signal from the frequency source 48 is in phase with the signal output of the detector as required. The undesired signals caused by factors previously described change at a slow rate in comparison with the switching frequency and are cancelled out. After passing through a low pass filter 56 that eliminates electrical noise above the frequency of the desired signals, the desired signals are applied to a recorder and integrator 58.

Although different types of detectors may be used, the detector 30 is illustrated as being of the thermal conductivity type wherein the characteristic being measured is the thermal conductivity of the gas passing through it. Sample gas and reference gas alternately flow into one end of a cavity 60 and out the other. The walls of the cavity are maintained at a reasonably uniform temperature by a block 64, but this block need not be as massive as in previous designs and good results have been attained with a block that weighs about 100 gms. The filament 62 is connected in series with a resistor 66 to form one side of a bridge circuit. The other side is formed by secondary windings 68 and 70 connected in series parallel relationship with the filament 62 and the resistor 66. The bridge can be energized with alternating current voltage of about 1 K Hz from a source 74 that is connected across the series combination of the primary windings 76 and 78 and held at a constant value by a regulator 80. The junction of the secondary windings 68 and 70 is connected to ground so that the amplitude of the alternating current voltage at the junction of the filament 60 and the resistor 66 varies as changes in the resistance of the filament 62 unbalance the bridge. The output of the bridge is applied to an amplitude modulation detector 50 which provides the output of the detector 30. Because the gases elute so slowly from the column 6, the concentrations represented by the peaks 12–18 require only 0.5 to 2.0 Hz to define them. Hence, the 10 Hz valve switching frequency is in effect a carrier that is amplitude modulated so as to have sidebands between 8 and 12 Hz. The 10 Hz carrier and its sidebands at the output of the detector 30 are applied to the synchronous detector 52.

In order to assist the filters which are usually included in the synchronous detector 52 in separating the desired sidebands from lower frequencies, it would be desirable to use a higher switching frequency, but the maximum operating frequency is limited by the response time of the fluid system. If the frequency is too high, a complete gas exchange will not occur. This would give an erroneous signal as the gas in the cavity 60 is a mixture of two gases. By using a sufficiently low switching frequency and by adjusting the delay 54, the synchronous detector 52 is a means for deriving a signal that is the difference between the signal at the output of the bridge when the cavity 60 is entirely filled with sample gas during one-half cycle of the switching frequency and a signal when the cavity is entirely filled with reference gas during the other half-cycle.

DESCRIPTION OF A PREFERRED EMBODIMENT

Figure 2:
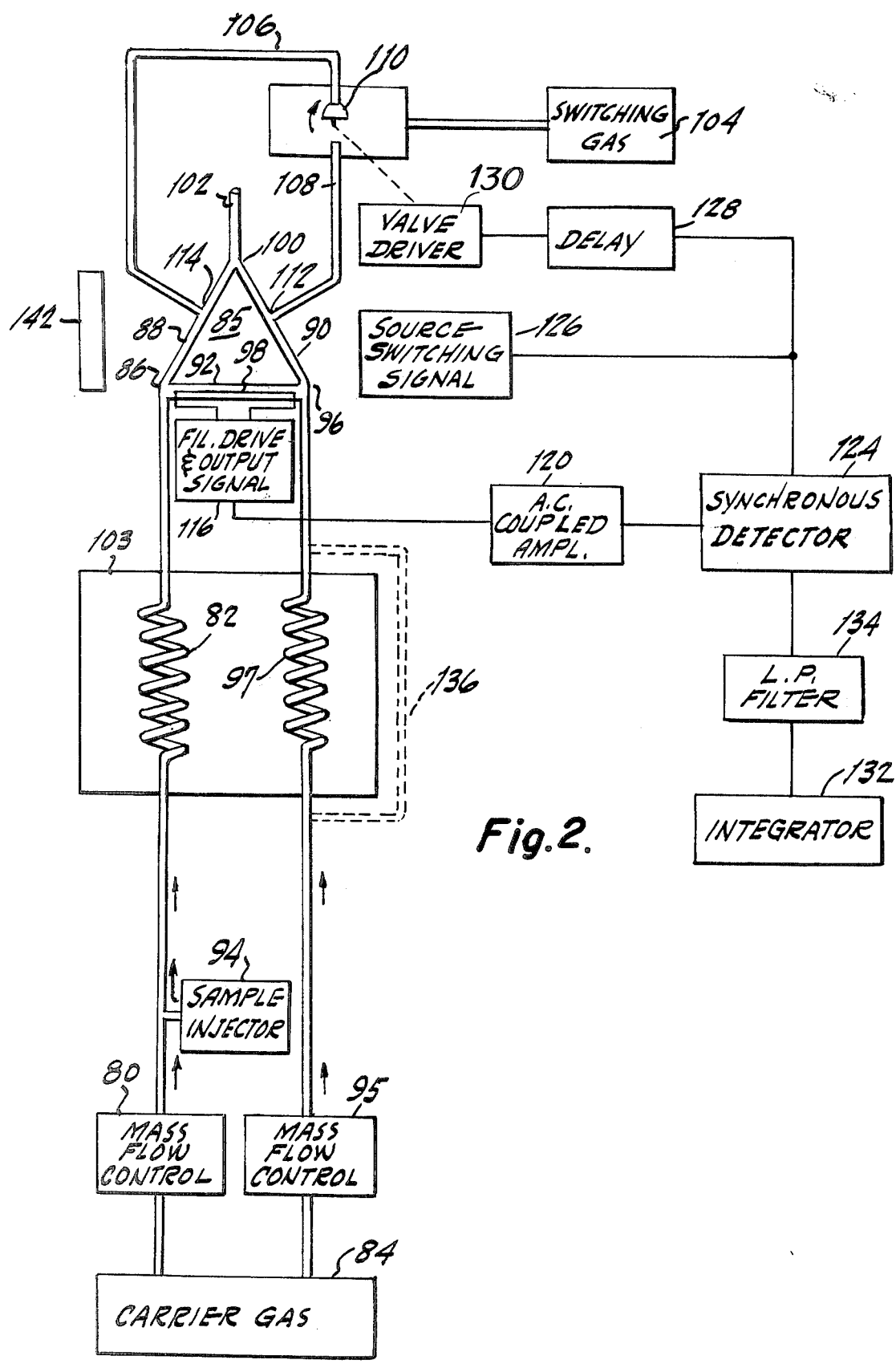

In FIG. 2 a gas chromatograph utilizing dual columns is illustrated in which the sample gas flows through the cavity of the thermal conductivity cell in one direction and reference gas flows in the other direction. The cell is so constructed that the final switching is accomplished by hydraulic means.

In particular a mass flow controller 80 and a column 82 are connected in series between a tank 84 of carrier gas and an access at the apex 86 of a closed triangular loop 85 comprised of three passageways 88, 90 and 92. Samples of a chemical to be analyzed are inserted into the stream of carrier gas at the input to the column 82 by a sample injector 94. A mass flow controller 95 is connected in series with the other column 97 between the tank 84 of reference gas and an access at the apex 96 of the loop 85 where the passages 90 and 92 meet. A filament 98 is mounted within the passageway 92. The passageways 88 and 90 may converge at the apex 100 to which a venting passageway 102 is connected as shown, or each may be connected to its own vent. Columns 82 and 97 are mounted in a temperature controlled oven 103.

Switching gas, which may be different than the reference or carrier gas, is supplied by a tank 104 and is applied to either tube 106 or tube 108 by a valve 110. When the valve blocks flow to the tube 106, as indicated in the drawing, the switching gas creates a pressure at the junction or switching access 112 of the tube 108 and the passageway 90. If that pressure is the same as the pressure at the apex 96, there is no flow between the points 96 and 112. In this event carrier gas from the column 97 flows through the passageway 92 past the filament 98 contained therein to the apex 86. From there it passes through the passageway 88 to the apex 100 and out the vent 102. Sample gas from the column 82 also flows to the vent 102 through the passageway 88. When the valve 110 is in the position opposite to that shown, switching gas in the tube 106 creates a pressure at the junction or switching access 114 of the tube 106 and the passageway 88 that can be equal to the pressure at the apex 86 so that no gas flows between the junction 114 and the apex 86. Accordingly the sample gas now flows through the passageway 92 and past the filament 98 to the apex 96 and thence to the vent 102 via the passageway 90. Thus sample gas and carrier gas alternately flow past the filament 98 in opposite directions. Actual experiment shows that this reduces the noise due to flowfluctuations to one eighth of that obtained in conventional systems. Theoretically we can account for about one half of this improvement.

Figure 1:
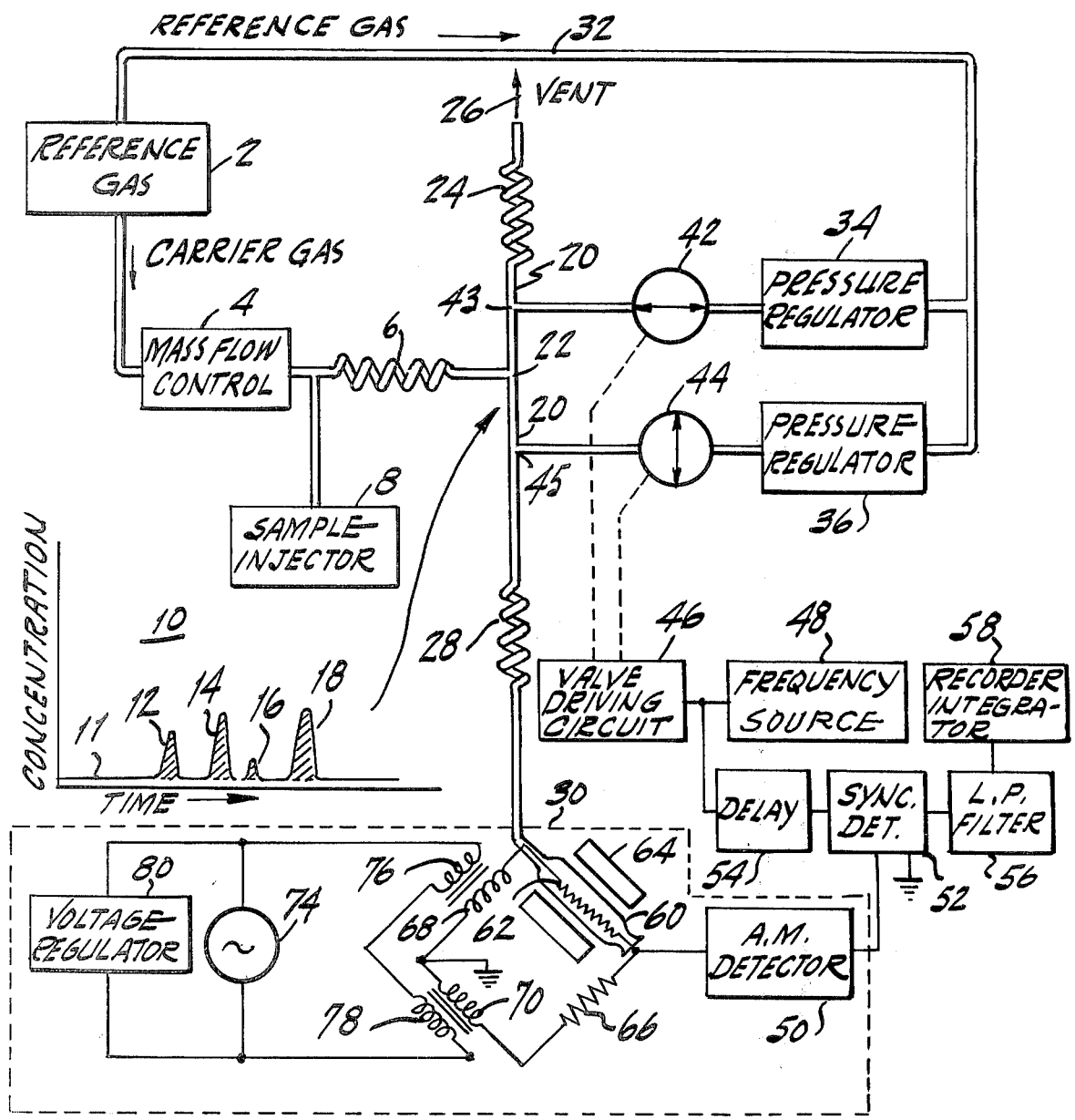

The filament 98 is connected to a filament drive and output signal drive 116 of any type well known to those skilled in the art but which may be like that illustrated in FIG. 1. The output signal is connected via an AC coupled amplifier 120 to a synchronous detector 124 wherein it is mixed with an alternating current voltage wave from a source 126. After passing through a delay means 128, alternating current voltage from the source 126 is applied to a valve drive 130 which rotates the valve 110 at the frequency of the source 126. If the delay means is properly adjusted, the phase of the signals applied to the synchronous detector 124 from the filament 98 will coincide with the phase of the signals applied to the detector from the source 126, thereby causing the output of the synchronous demodulator to accurately represent the difference between the signals produced by the filament 98 when sample gas flows over it and the signal produced by the filament 98 when carrier gas flows over it. The output signal of the synchronous detector 124 is applied to an integrator 132 via a low pass filter 134 that eliminates signals above 2 Hz.

It will be noted that the use of switching gas confines the sample gas to the triangular groove 85 so that the valve 110 cannot be deteriorated by the sometimes corrosive sample gas. Another advantage of this arrangement is that if the flow through the column 82 is very low, the switching gas can augment the flow through the cell to allow higher frequency operation. It therefore becomes what can be termed makeup gas, but when operated in this way the switching gas must be the same as the carrier gas.

With the arrangement just described, the temperature of the oven 103 may be programmed as previously mentioned in order to provide better separation between the intervals when the chemical consitituents of the sample gas injected by the injector 94 reach the output of the column 82. Carrier gas flows through the column 97 and appears at its output with the same amount and kind of "bleed" constituents that appear at the output of the sample column 82. Hence, in either half-cycle of the switching frequency the "bleed" constituents produce the same effect on the filament 98 and cause it to produce the same baseline signal. However, the sample constituents from the column 82 cause a difference in the effect on the filament 98 and in the signal it produces during one half of each switching cycle. This difference is detected by the synchronous detector 124. Other means could be used to derive the difference in the signals produced by the filament 98 during successive half-cycles of the switching signal. Inasmuch as the difference in signals produced by the filament 98 is the only thing of importance, factors like ambient temperatures that change slowly have little effect. Hence, the weight of the thermal block shown diagramatically at 142 can be significantly reduced.

If the chemicals in the sample being analyzed do not require the temperature of the oven 103 to be programmed in order to attain better separation at the output of the column 82, single column operation is possible, but once again factors that vary slowly with respect to the switching cycle can be cancelled out if the operation is the same as just described, i.e., both columns 82 and 97 are operative. However, if a second column is not available, or if the chromatograph does not have provision for one, advantageous single column operation can be achieved by passing the carrier gas directly from the tank 84 to the detector via the dotted tube 136.

It will be understood by those skilled in the art that any type of detector could be used in place of the thermal conductivity detector shown in FIG. 1. Furthermore, although the invention has been described as it would be used in a gas chromatograph, the concept of alternately supplying a detector with a carrier medium containing a sample and a carrier medium alone can be applied to any fluid stream detector.

Reference is now made to FIGS. 3, 3A and 3B for a description of one type of construction of a thermal conductivity detector useful in this invention. The detector is formed from two metal plates 144 and 146 which are shown rotated to an open position in FIG. 3, as indicated by the arrow 147, so that the interior surfaces can be seen. The plate 144 has a planar surface except for a groove 148 in the form of a triangle. Holes 150 and 152 extend from the groove 148 through the plate 144 and are respectively connected to tubes 154 and 156 that are in turn adapted to be respectively connected to the columns 82 and 97 of FIG. 2. Holes 158 and 160 extend from the groove 148 through the plate 144 and are respectively adapted to be connected to tubes 106 and 108 of FIG. 2. A hole 162 extends from the groove 148 through the plate 144 and is adapted to be connected to the vent tube 102 of FIG. 2.

The upper plate 146 has a planar inner surface except for a groove 162 that is located so as to overlie the portion of the groove 148 in the plate 144 that extends between and includes the holes 150 and 152. Posts 164 and 166 of electrically conducting material are electrically insulated from the plate 146 and extend into the ends of the groove 162. A filament 170 of resistance wire is attached to the ends of the posts 164 and 166 so as to lie substantially in the plane of the inner surface of the plate 146. This construction is illustrated in more detail in FIG. 3C which is a section CC of FIG. 3B. The location of BB is also indicated in FIG. 3. FIG. 3A is an outer perspective view of the plates with their inner surface in contact as intended when in use. The plates 144 and 146 are held together by bolts 172 that extend through the aligned holes 172' and 172" in the plates.

The groove 148 forms a passageway in the form of a closed loop.

Good performance of the detector demands symmetry so that the hydraulic impedances between the vent and each of the points of application of the switching gas are the same. The hydraulic impedance between the vent and each of the points of application of the sample gas and the carrier gas are also the same. The groove can follow any path, but whatever the configuration, it can be fabricated by using two plates corresponding to the plates 144 and 146.

FIG. 4 illustrates a way in which this invention can be used to monitor the flow of gas in a pipeline 178. A small sample of the gas in the pipeline is supplied to one end of a thermal conductivity detector 180, via a tube 182 and a flow control 184. Reference gas is supplied from a tank 186 to the other end of the detector 180 via a tube 188 and a flow control 190. Both tubes 182 and 188 extend beyond the detector 180 to a mechanical switching means 192 that can be actuated in any suitable manner to alternately block the ends of the tubes 182 and 188. When the switching means 192 blocks the tube 182, gas from the pipeline 178 flows through the detector 180, and when the switching means 192 blocks the tube 188, the reference gas flows through the detector. If the reference gas is the same as the gas that flows in the pipeline 178, the signals produced by a filament drive and output circuit 194 during each position of the switching means 192 will be the same, so that the difference signals provided by the synchronous detector 198 will be zero. If, however, the constituents of the gas in the pipeline change, the signals produced by the filament drive circuit 194 during each position of the switching means 192 is different so that the signal provided to the synchronous detector 198 is an alternating current wave having a frequency equal to the frequency at which the switching means 192 operates and an amplitude determined by the difference between the gas in the pipeline 178 and the reference gas in the tank 186 that is used as a standard. Alternatively, an arrangement such as shown in FIG. 1 could be used wherein the gas from the pipeline 178 is substituted for effluent from column 6 and the reference gas is used to perform the switching action. It is also contemplated that other types of detectors could be used in either arrangement.

The arrangement of FIG. 4 can also be used as a leak detector by placing the end of the tube 182 that is connected to the pipeline 178 near a point where a leak is being investigated and by placing the end of the tube 188 that is connected to the source 186 of reference gas in nearby ambient air. Any suitable means may be used to cause a flow through tubes 142 and 146 to the switching means 148.

Although FIGS. 1 and 2 illustrate the application of the invention to gas chromatographs, certain aspects of the invention can be applied to liquid chromatographs as well. Carrier gas serves the same function in gas chromatographs as carrier liquid in liquid chromatographs and each can be referred to as a carrier medium. The sample of chemical being analyzed is in gaseous form in a gas chromatograph and in liquid form in a liquid chromatograph, but each can be referred to as a sample. The function of the column in either gas or liquid chromatographs is the same, i.e., to separate the intervals at which different chemicals in the sample emerge from it. In each type of chromatograph the detectors are responsive to the intensity of a given characteristic of the matter flowing through them and the amount of each chemical in the sample is derived by integrating the output of this detector. Dual detector operation is performed in both liquid and gas chromatographs in order to eliminate the effects of baseline drift in the manner described. Use of this invention not only permits more accurate elimination of this drift with a single detector but it also eliminates errors due to mismatch of the two detectors previously used. In single column operation, the invention provides for better performance because errors due to the detector itself can be largely eliminated by switching the flow through the detector, between the output flow of a sample column and a flow of carrier medium.

Application of the invention to both dual column operation and single column operation of gas chromatographs employing therman conductivity detection is especially advantageous because it permits the construction of a lighter and far less expensive detector as well as the attainment of accurate measurements with a much shorter stabilization time.

Although only one sample stream and one reference stream are shown, multiple streams of each could be used. Various means could be employed to derive signals representing the relationships among sample and reference streams by measuring the detector response to the streams in an appropriate sequence.

One aspect of the invention, namely the alternate flow of carrier gas and column effluent through the thermal conductivity detector in opposite directions, reduces the amount of noise due to column flow variations, in the output signal eight times as much as would be expected in a conventional system and twice as much as theory predicts.

What is claimed:

1. In combination
   a thermal conductivity cell comprising means defining a cavity and a filament mounted therein,
   means for heating said filament,
   means adapted to cause alternate flows of reference fluid and a mixture of carrier and sample fluids through said cavity at a given frequency,
   means for deriving an electrical signal from said filament that corresponds to the instantaneous power drawn from said filament by the alternate presence in the cavity of said reference fluid and the fluid that is a mixture of said carrier and sample fluids and
   means for deriving an output signal proportional to the peak to peak amplitude of said electrical signal.

2. The combination as set forth in claim 1 wherein the given frequency is higher than the frequency of undesired signals.

3. The combination as set forth in claim 1 wherein the given frequency is greater than twice the highest signal frequencies.

4. In combination
   a thermal conductivity cell comprising means defining a cavity and a filament mounted therein,
   means for heating said filament,
   means adapted to cause alternate flow of reference fluid and sample fluid through said cavity in opposite directions at a given frequency,
   means for deriving an electrical signal from said filament that corresponds to the instantaneous power drawn from said filament by the alternate presence of said reference and sample fluids in the cavity, and
   means for deriving an output signal proportional to the peak to peak amplitude of said electrical signal.

5. A thermal conductivity cell comprising means defining a cavity,
   a filament,
   means supporting said filament in said cavity,
   a first passageway communicating with said cavity at a first point,
   a second passageway communicating with said cavity at a second point, said first and second points being so located with respect to said filament that fluid passing through said cavity from said first passageway passes by said filament in one direction and fluid passing through said cavity from said second passageway passes by said filament in the opposite direction,
   a third passageway communicating with said cavity at a third point, said third point being so located that fluid can pass from said first passageway to said third passageway without passing by said filament, and
   a fourth passageway communicating with said cavity at a fourth point, said fourth point being so located that fluid can pass from said second passageway to said fourth passageway without passing by said filament.

6. A thermal conductivity cell as set forth in claim 5 wherein
   said third passageway has means defining an opening at an intermediate point along it, and
   said fourth passageway has means defining an opening at an intermediate point along it.

7. In a chromatograph the combination of a first passageway in communication with a vent at both ends,
   a column communicating with said passageway at a given intermediate point,
   second and third passageways communicating with said first passageway at points on either side of the given point at which said column communicates with said first passageway,
   means for alternating flow of reference gas through said second and third passageways and into said first passageway at a given frequency,
   and a detector inserted in said first passageway between a vent and the point at which said second passageway communicates with it.

8. The combination as set forth in claim 7 wherein said given frequency is higher than the frequency of undesired signals.

9. The combination as set forth in claim 7 wherein said given frequency is higher than 2.0 Hz.

10. A thermal conductivity cell comprising
    first and second plates having planar juxtaposed surfaces in contact with each other,
    means defining a groove in at least one of said surfaces,
    a filament mounted in said groove and spaced from said plates,
    electrical conductors connected to opposite ends of said filament,
    means defining first and second openings respectively communicating between a point outside said plates and said groove at points on opposite sides of the center of said filament,
    means defining third and fourth openings respectively communicating between a point outside said plates and said groove at points on opposite sides of the center of said filament, means defining third and fourth openings respectively communicating between a point outside said plates and said groove at points on opposite sides of the center of said filament and farther from the center of said filament than the points at which said first and second openings communicate with said groove, means including at least one opening respectively communicating between a point outside of said plates and said groove at points on opposite sides of the center of said filament and farther from the center of said filament than the points at which said third and fourth openings communicate with said groove.

11. In a chromatograph, the combination of means for injecting samples of matter to be analyzed into a flow of carrier medium so that a mixture of said samples and said carrier medium appears at its output, first coupling means at the output of said injecting means to which one end of a chromatographic column may be attached, second coupling means to which the other end of a chromatographic column may be attached, third coupling means to which a source of reference medium may be connected, a thermal conductivity detector for producing electrical signals corresponding to the thermal conductivity of matter flowing through it, switching means for alternately coupling said second and third coupling means to said detector, and means for deriving a signal representing the difference between the signal produced by said detector in response to matter flowing through it from said second coupling means and the signal produced by said detector in response to matter flowing through it from said third coupling means.

12. In a chromatograph, the combination of means for injecting samples of matter to be analyzed into a flow of carrier medium so that a mixture of said samples and said carrier medium appears at its output, first coupling means at the output of said injecting means to which one end of a chromatographic column may be attached, second coupling means to which the other end of a chromatographic column may be attached, a chromatographic column having one end coupled to said first coupling means and the other end coupled to said second coupling means, third coupling means to which a source of reference medium may be connected, a thermal conductivity detector for producing electrical signals corresponding to the thermal conductivity of matter flowing through it, switching mean for alternately coupling said second and third coupling means to said detector, and means for deriving a signal representing the difference between the signal produced by said detector in response to matter flowing through it from said second coupling means and the signal produced by said detector in response to matter flowing through it from said third coupling means.

13. In a chromatograph wherein the elutant from a chromatographic column is comprised of a flow of carrier medium containing concentrations of chemicals different from said carrier medium so that mixture of the carrier medium and the respective chemicals appear within finite spaced periods of time and wherein the amount of the chemicals in each concentration is to be determined by comparing the intensity of a given characteristic of the concentration of chemicals with the intensity of the same characteristic of a reference medium, the combination of a thermal conductivity detector that produces an output signal that represents the thermal conductivity of matter flowing through it, switching means for changing the flow through said detector from the elutant of a chromatographic column to a reference medium at a sufficiently fast rate so that a plurality of changes occur during the finite periods when the concentration of chemicals appears in the elutant from the chromatographic column, and means for deriving from the signals produced by said detector an output signal representing the difference between the value of the output signal of said detector when the elutant from a chromatographic column is flowing through it and the value of the output signal of said detector when the reference medium is flowing through it, said output signal thereby representing the amount of the chemicals in each concentration.

14. The combination as set forth in claim 13 wherein said detector is a thermal conductivity detector comprised of a single cell.

* * * * *